(12) United States Patent
Crumly et al.

(10) Patent No.: US 6,849,168 B2
(45) Date of Patent: Feb. 1, 2005

(54) ELECTROCHEMICAL MICROSENSOR PACKAGE

(75) Inventors: William F. Crumly, Anaheim, CA (US); Marc J. Madou, San Diego, CA (US)

(73) Assignee: KVAL, Inc., Petaluma, CA (US)

( * ) Notice: Subject to any disclaimer, the term of this patent is extended or adjusted under 35 U.S.C. 154(b) by 529 days.

(21) Appl. No.: 10/014,892

(22) Filed: Nov. 9, 2001

(65) Prior Publication Data

US 2002/0121439 A1 Sep. 5, 2002

Related U.S. Application Data

(60) Provisional application No. 60/248,083, filed on Nov. 13, 2000.

(51) Int. Cl.[7] .................. G01N 27/333; G01N 27/28; C25D 1/00; B32B 31/00
(52) U.S. Cl. .................. 204/416; 204/431; 156/151; 156/249
(58) Field of Search ................. 204/403.01, 403.1, 204/403.13, 403.14, 404, 405, 416, 431; 205/191; 156/150, 151, 249

(56) References Cited

U.S. PATENT DOCUMENTS

| | | | |
|---|---|---|---|
| 3,768,259 A | * | 10/1973 | Carnahan et al. ............. 60/276 |
| 4,765,864 A | | 8/1988 | Holland et al. |
| 4,812,221 A | | 3/1989 | Madou et al. |
| 4,874,500 A | | 10/1989 | Madou et al. |
| 4,900,405 A | | 2/1990 | Otagawa et al. |
| 5,018,527 A | * | 5/1991 | Pfab et al. .................. 600/348 |
| 5,056,216 A | | 10/1991 | Madou |
| 5,183,549 A | | 2/1993 | Joseph et al. |
| 5,197,184 A | | 3/1993 | Crumly et al. |
| 5,207,887 A | | 5/1993 | Crumly et al. |
| 5,308,469 A | * | 5/1994 | Aldinger et al. ............ 204/426 |
| 5,364,277 A | | 11/1994 | Crumly et al. |
| 5,607,566 A | * | 3/1997 | Brown et al. ............... 257/414 |

OTHER PUBLICATIONS

Zirconium oxide entry in Hawley's Condensed Chemical Dictionary, 14th edition, 2002, John Wiley & Sons, Inc.*
CAPLUS abstract of Hobbs, "DGO formation by lateral oxidation," IP.com Journal (2002), 3(11), 2 (No. IPCOM000008808D), Jul. 1, 2002.*

* cited by examiner

Primary Examiner—Alex Noguerola
(74) Attorney, Agent, or Firm—Corwin R. Horton

(57) ABSTRACT

An electrochemical microsensor package comprises a substrate matrix having a upper non-conductive layer and an adjacent lower non-conductive layer with a conductive trace or pad extending over an area therebetween. The conductive pad has integral therewith a projecting contact button that projects through and below the second non-conductive for making contact with external electrical contacts. A sensor electrode is positioned on the surface of the conductive pad toward the upper non-conductive layer and in electrical contact therewith. A well extends through the upper non-conductive layer to the upper surface of the electrode. The microsensor packages may be produced by electrodeposition of the conductive pad onto a conductive mandrel having depressions to form the contact button.

The microsensor package is fabricated into a microsensor by appropriate adaptation of the well of the microsensor package including applying an appropriate oxide or other layer over the electrode, introduction of an electrolyte or other sensing chemicals into the well and or applying a permeable or impermeable membrane over the top of the well.

42 Claims, 3 Drawing Sheets

ELECTROCHEMICAL MICROSENSOR PACKAGE

This application claims the benefit of U.S. Provisional Application No. 60/248,083, filed on Nov. 13, 2000.

BACKGROUND OF THE INVENTION

This invention relates to electrochemical microsensors and particularly to structures or packages which may be advantageously utilized for the manufacture of a wide variety of miniature or "micro" sensors. This invention also relates to methods for the manufacture of such microsensors and packages therefor. Electrochemical microsensors have a wide range of existing and potential uses in various arts for chemical detection and measurement, especially in biochemical applications such as in medicine. In order to succeed in the point of care market, the biosensor systems must meet their application needs. Planar electrochemical sensors with microelectronic production techniques are known as an elegant approach to meet these requirements. Due to the batch processing and high precision of microelectronic techniques, the miniaturized planar sensors have major advantages including small dimension, low cost per sensor, high reproducibility and the possibility of smart sensor realizations.

In the past few years, a number of micro-fabricated sensors have been designed and developed by microelectronic techniques as exemplified in U.S. Pat. No. 4,874,500. These sensors are usually fabricated by opening wells in a silicon chip using IC technologies and filling the wells with sensing chemicals. The bottoms of the wells are typically coated with silver and the surface of the silver converted to silver chloride. Then a hydrogel containing a known concentration of chloride ions is placed into the well on top of the silver chloride, creating a known electrochemical potential between the hydrogel and the silver chloride electrode. The well is then covered with a membrane that has in it chemical that effects the attraction of the target ion. An electrochemical potential is developed between the silver and the unknown liquid through the hydrogel that depends on the relative concentration of the target ion between the membrane and the target liquid, which is determined by the concentration of the target ion in the target liquid. The are usable for detecting various ions as well as gases. However, in these cases, silicon is only a substrate and does not play any role in the sensing mechanism itself. Using silicon to make the wells is expensive. Multiple sensors on the same chip are incompatible requiring wide separation which in turn, causes low yields and large chip sizes. Low yields and large chip sizes combined with expensive fabrication processes causes the finished product to be costly. Our alternative avoids these problems and also uses inexpensive materials and processes for an order of magnitude cost advantage. There also exist some problems concerning the final package of the sensors because a chemical sensor on an insulating substrate is almost always easier to package than on a piece of silicon with conductive edges in need of insulation. Moreover, many chemical sensor materials are incompatible with IC processing; therefore the very point of using silicon is forfeit for many chemical sensors.

For connection with associated electronics, such microfabricated sensors have relied upon a conductor extending from the sensor well that is on the same surface as the opening in the sensor well. Placing such pins so they made good electrical contact while at the same time not damaging the sensor is difficult. Alternatively, wire bonding is used to make electrical connection to the conductor on the sensor. The completed assembly is delicate and easily broken. Also, since the hydrogel in the microsensors are vulnerable to elevated temperatures, soldered connections are not a viable option. A more robust construction would be to bring the electrode connection out of the sensor well to the side of the sensor opposite from the opening in the sensor well itself. Such a construction is difficult to achieve using silicon fabrication techniques.

Pressure type electrical contact buttons are described in U.S. Pat. Nos. 5,364,277, 5,197,184 and 5,207,887 which are formed integrally with an electrical trace fixed on a substrate and which project through and outwardly of the substrate for make contact by pressing against another contact element. However, these contacts are for employment as terminal connections for wire cable terminations and there is no suggestion that these contacts could have any utility for electrochemical microsensors or how they might be adapted to be employed therewith. Lately, flexible polyimide film (Kapton) has been used as a substrate in microfabricated planar sensor arrays. Photolithography and sputtering technologies are used in the fabrication of the sensor arrays. These sensor arrays have shown good analytical properties for in-vivo measurements and have solved the problems with respect to membrane optimization, adhesion of membrane to its substrate, etc., but the sputtering process causes the fabrication of sensors to be expensive and time consuming

SUMMARY OF THE INVENTION

This invention relates to a new design and fabrication process for miniaturized electrochemical sensors and packages therefor. In this design, miniaturized electrochemical sensors, may be fabricated on sheets of a non-silicon material substrate by a batch, modular-manufacturing methodology.

Microsensor packages produced in accordance with this invention may be charged with electrolytic media or analytes appropriate to the desired sensor or electrode end use. The individual devices may then be separated from the sheet and then integrated into appropriate combinations or systems, such as multiple analyte sensor arrays, using pick and place technology. By fabricating identical miniaturized devices on a single large sheet of substrate the yield substantially increases over conventional substrates.

The microsensor packages of this invention comprise a laminated substrate of a first and a second non-conductive layer having a conductive trace that extends over an area of their interface. A sensing electrode is also located at the interface adjacent to and in electrical contact with the conductive trace. A sensor well is provided in the first conductive layer at the location of the electrode that extends from the upper surface thereof downward to the electrode to expose the electrode for electrochemical sensing. The conductive trace is provided with a three-dimensional conductive contact portion, formed integrally therewith, that projects through and outwardly of the second non-conductive layer to provide an external pressure interconnection with other electrical elements. As appropriate to the end use of the microsensor desired, a membrane may be applied at the exposed surface of the first non-conductive layer to enclose the well. The membrane may be provided with one or more small holes or pores at well to provide fluid communication with the well to and from the outside, as appropriate to the end use desired.

In this invention microsensor packages are fabricated by a low cost methodology which comprises forming a generally planar conductive trace having an integral three-dimensional contact portion in the form of a projection or button that projects outwardly from the plane of the trace. A sensor is then affixed to the trace at the side opposed to the projection. A non-conductive layer having an opening to accommodate the projection of the trace is laminated to the projection side of the trace and another non-conductive layer having a opening to form a well above the electrode is laminated to the electrode side of the trace.

As another feature of the invention, the microsensors may be manufactured with electrodeposition techniques utilizing an electroconductive mandrel having a pattern of depressions on its surface. A coating of conductive material is first electrodeposited on the mandrel to form a conductive trace for each of a series of sensor package to be produced. The traces will each bear integrally formed projections at the depression sites. An electrode is then formed on each conductive trace. A non-conductive substrate having holes which are appropriately spaced to register with the respective electrodes is then laminated to conductive traces. This structure is then removed from the mandrel and a second non-conductive substrate having holes which register with projections on the traces is then laminated to the trace side of the structure.

BRIEF DESCRIPTION OF THE DRAWINGS

The invention will be better understood by reference to the figures of the drawings wherein like numbers denote like parts throughout and wherein.

DETAILED DESCRIPTION OF THE PREFERRED EMBODIMENT

The following description illustrates the manner in which the principles of the invention are applied but is not to be construed as limiting the scope of the invention.

The present invention provides for structures or "packages" for electrochemical sensors which will give them improved connectability and reliability. In accordance with this invention these packages may be produced at low cost by batch, modular-manufacturing methodology. With this methodology of this identical miniaturized fluidic devices may be fabricated on a single large sheet with a yield substantially increased over conventional substrates. The individual devices may then be separated and used individually or placed in arrays, such as to produce multiple analyte sensor arrays, using pick and place technology.

The sensor packages of this invention have a non-conductive matrix in which is provided a sensor well for containing sensing chemicals and a sensing electrode at the bottom of the well. A conductive trace is located in the matrix that extends to the electrode to make electrical contact therewith. The conductive trace may be provided with a integral three-dimensional element that projects to the outside of the matrix where it is available to make interconnection with other electrical elements in order to transmit signals from the sensor thereto.

The microsensor packages of this invention may be manufactured in many ways. The various individual steps in the fabrication of the sensor packages of this invention, per se, are well known in the art. These may include photolithography, use of photomasks and silk screening and other printing techniques, lamination of films or resists to substrates and design of specific sensors for specific applications, Literature available on these subjects include the text *Fundamentals of Microfabrication*, M. Madou, CRC Press, Boca Raton, 1997, the disclosures of which are incorporated herein by reference.

Figure 1:
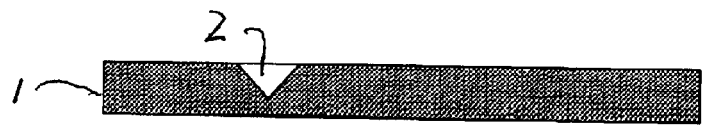
FIG. 1 illustrates, in a side sectional view, a mandrel employed for preparation of a microsensor package of this invention.
Figure 2:
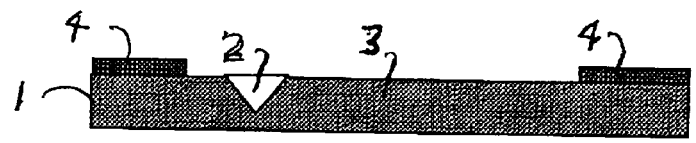
FIG. 2 is the same view as in FIG. 1 after deposition of a resist on the mandrel surface and development thereof to expose a microsensor pad forming area.
Figure 3:
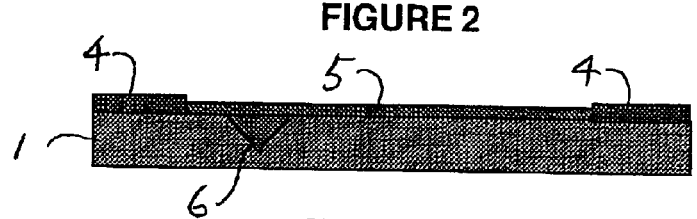
FIG. 3 is the same view as in FIG. 2 after electrodeposition of a conductive layer on the mandrel for the sensor package.

There are various methods of fabricating the microsensor packages of this invention. FIGS. 1 through 7 illustrate a highly advantageous method for the fabrication of a typical microsensor package of this invention utilizing electrodeposition on a preformed mandrel to form a series of identical sensor packages at the same time on the mandrel surface. The mandrel may be prepared as described in U.S. Pat. No. 5,197,184 to Crumly et al. A stainless steel mandrel 1 is prepared with pre-drilled dimples or depressions 2 corresponding to the locations for projecting contacts for the individual sensor packages as shown in FIG. 1 for a area of the mandrel for forming one of the sensor pads. Photoresist is applied to the mandrel, and openings created therein corresponding to the sensor pads by photolithographically developing the photoresist to leave an uncovered area in the resist 4. as seen in FIG. 2. Copper is then electrolytically deposited into the openings 4 in the photoresist to form a conductive trace in the form of a pad 5 and the raised contact or projection 6 integral therewith simultaneously as shown in FIG. 3. The trace or pad 5 is typically desired in the form of a foil or sheet for ease in forming an electrode thereon and for supporting same, as will be described. Desirably, pad 5 will extend co-extensively.

Figure 4:
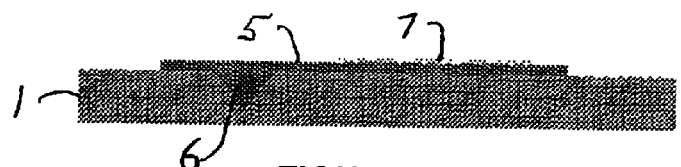
FIG. 4 is the same view as in FIG. 3 after an electrode has been formed on the upper surface of the conductive layer.

The photoresist is stripped and then sensing electrode 7 is created on conductive layer or pad 5 as shown in FIG. 4 as by silkscreening silver epoxy ink, such as DuPont type 5504, onto the surface of copper layer 5. Desirably, the bottom side of electrode 7 and the upper side of pad 5 are coextensive in order to better support the electrode and provide good electric contact. Silver is important for use as electrode because it is compatible with an entire class of sensing chemistries that are readily available However, other electrode materials may be employed, for example, gold, paladium, nickel, platinum, iridium, their oxides and combination thereof, as appropriate for the particular microsensors to be constructed from the microsensor packages.

Figure 5:
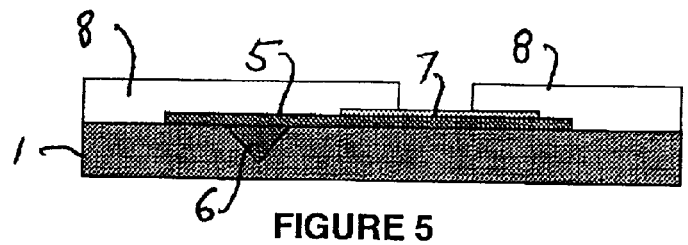
FIG. 5 is the same view as in FIG. 4 after lamination of a non-conductive layer onto the conductive layer.
Figure 6:
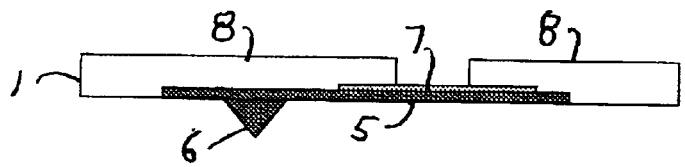
FIG. 6 illustrates, in a side sectional view, the microsensor package construct of FIG. 5 after it has been removed from the mandrel.
Figure 7:
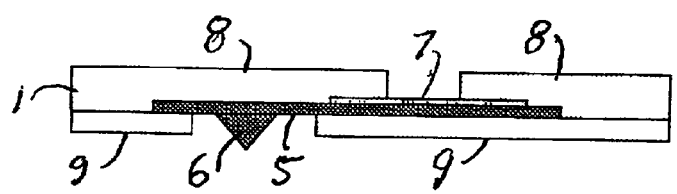
FIG. 7 is the same as in FIG. 6 after lamination of a second non-conductive layer onto the microsensor package construct.

A coverlay of non-conductive material, such as Kapton film, which has been predrilled with holes corresponding to the locations for the sensor wells (over the electrodes) and coated on the underside with adhesive, such as Pyralux adhesive, is laminated onto the exposed surface of conductive layer 5 and electrode 7 to form non-conductive layer 8 as shown in FIG. 5. The well holes in non-conductive layer 8 are configured and placed so that layer 8 completely captures the edges of electrode 7 when it is laminated in place. This prevents any leakage of the sensing current around the electrode. The microsensor package construct is now removed from the mandrel, exposing conductive layer or pad 5 and projection 6 as seen in FIG. 6. Referring to FIG. 7, Kapton film or other non-conductive sheet material which has been predrilled with holes corresponding to the locations of projections 6 and coated with adhesive may be laminated onto the raised contact side of the package to create the second non-conductive layer, if desired, and thereby complete the microsensor package.

Figure 8:
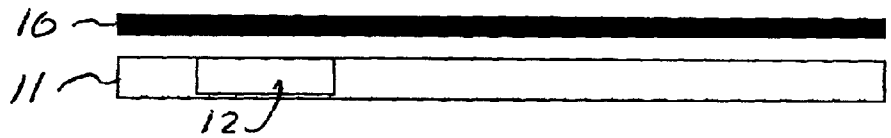
FIG. 8 illustrates, in a side sectional view, a conductive copper sheet and a non-conductive sheet which are to be laminated together.
Figure 9:
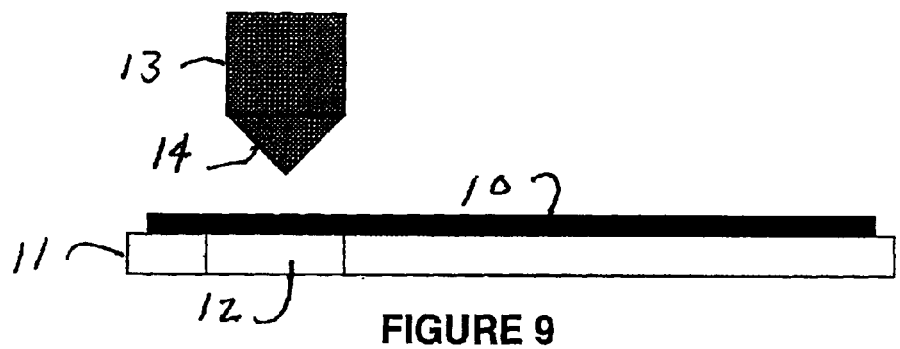
FIG. 9 is the same view as FIG. 8 after lamination of the sheet and showing, in side sectional view, an embossing tool to be applied to the laminate.
Figure 10:
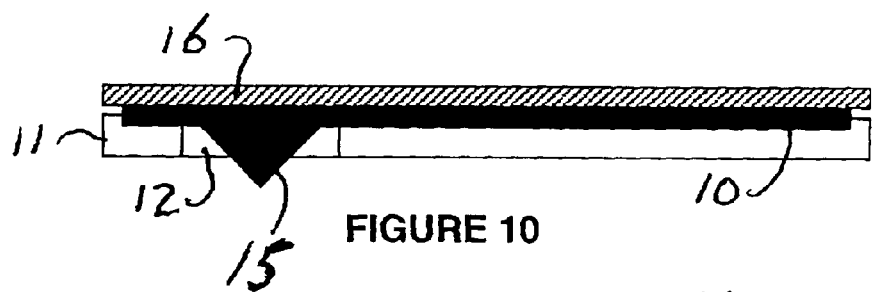
FIG. 10 is the same view as FIG. 9 after the laminate has been embossed to create a projecting contact and the laminate has been coated with a resist.

FIGS. 8 through 12 illustrate another method for fabricating microsensor packages of this invention. Referring to FIG. 8, a copper foil or sheet is employed to form the conductive layer or trace 10 and a non-conductive sheet, such as of Kapton, is employed as non-conductive layer 11. Sheet 11 has been predrilled to form a opening 12. Sheets 10 and 11 are laminated together, utilizing Pyralux adhesive or the like as shown in FIG. 9. An embossing tool 13 with a conical point is applied against the upper side of layer 10 at the site of opening 12 in layer 11 to form a dimple in conductive layer 10 that protrudes through hole 12 as shown in FIG. 10.

Figure 11:
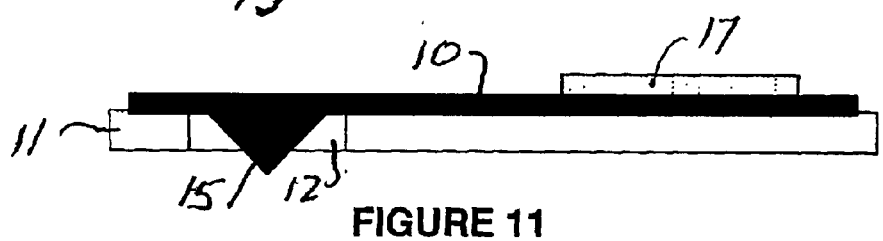
FIG. 11 is the same view as FIG. 10 after an electrode has been deposited on the laminate and the resist removed.
Figure 12:
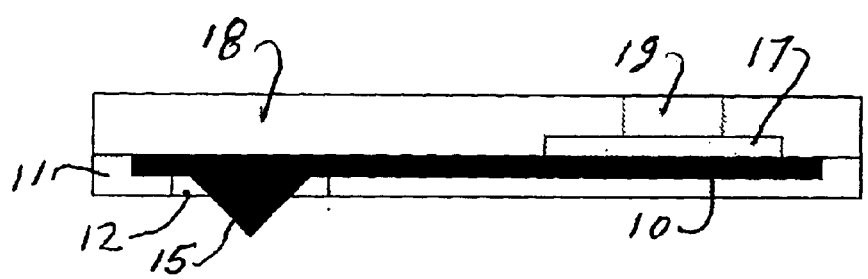
FIG. 12 is the same view as FIG. 11 after lamination of a non-conductive coverlay onto the laminate.

Photoresist 16 is then applied to the exposed upper surface of conductive layer 10. The resist is photo-exposed with the pattern for an electrode to be deposited on the surface and then the resist is developed to expose the area on the surface for etching and then depositing of the electrode. The surface is then etched and an electrode 17 formed on the surface, as by deposition of a silver epoxy ink, such as DuPont type 5504, as shown in FIG. 11. A coverlay of non-conductive material, such as Kapton film, which has been predrilled with holes corresponding to the locations for the sensor wells (over the electrodes) and coated on the underside with adhesive, such as Pyralux adhesive, is laminated onto the exposed surface of conductive layer 10 and electrode 17 to form non-conductive layer 18, as shown in FIG. 12.

Other conductive metals may be employed for forming or overplating the conductive trace 5 and contact 6, as for example silver, gold, paladium and nickel. It may advantageous in some cases to use a metal such as silver which can serve as both the conductive layer and the electrode at the well location, thus obviating the need to fabricate a separate electrode at the well.

In the embodiments shown, the raised contact buttons or projections of the conductive layer are offset from the well, in the plane of the non-conductive layers, rather than extending to and below the sensor package directly below the well. This may be desirable for ease of fabrication and to minimize the possibility for damage to the sensor if pressure for securing an electrical contact below the sensor is applied directly over the well. However, in an alternate design of sensor package, the raised contact button may be placed immediately below the well in order to further miniaturize the sensor.

It will be understood that utilizing the foregoing procedure a multiplicity of identical structures may be fabricated at the same time across the surface of the laminate formed as shown in the preceding examples Microsensors of this invention may then be produced from the microsensor packages by appropriate adaptation of the well of the microsensor package for the desired purpose for the microsensor. This may include the formation of an appropriate oxide or other layer over the electrode, introduction of an electrolyte or other sensing chemicals into the well. It also may include the application of a permeable membrane over the top of the well so as to retain the contents of the well while permitting communication thereto of gases or liquids for analysis.

For a microprocessor package with a silver electrode, the surface of the silver electrode may be converted to silver chloride to produce a sensor sensitive to chloride. Other various sensing chemistries may require different surface finishes on the electrode to react properly (or not react in the case of an inert surface). For instance some enzyme chemistries (and other biological assays) would work best if the electrode or the surface thereof in the well is coated with gold or platinum. Other electrochemical systems may be developed from time to time, which would require a different surface material at the bottom of the well. This will not change the basic microprocessor package.

Figure 13:
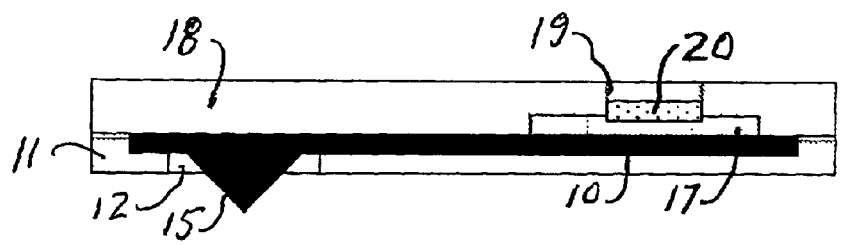
FIG. 13 is the same view as in FIG. 12 after treatment of the electrode surface in the well to create a silver chloride layer.
Figure 14:
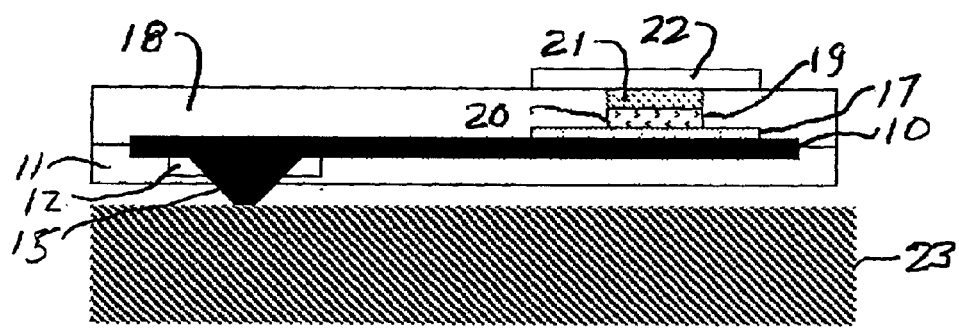
FIG. 14 is the same view as in FIG. 13 after deposition of electrolyte medium in the well and depositing of a membrane on the upper surface of the microprocessor package over the well.

Starting with the microsensor package described above, and particularly the package depicted in FIG. 12, a microsensor for detecting the chloride ion can be fabricated as shown in FIGS. 13 and 14. The exposed surface of silver electrode 17 in well 19 is chloridized with $FeCl_3$ solution to form the silver chloride layer 20 as seen in FIG. 13. Well 19 is then filled with an electrolytic medium 21 as seen in FIG. 14. The electrolytic medium can be a liquid but more preferably is in the nature of a hydrogel or a solid polymer electrolyte.

After well 19 has been charged with electrolyte medium 21, a membrane 22 is deposited over the top of well 19 to complete the microprocessor as seen in FIG. 14. Membrane 23 may be a microporous membrane or otherwise contains suitable openings for fluid communication into the well 19 as suitable for the particular sensor. A non-porous plasticized polymeric membrane is normally used for covering potentiometric elements. Ion-selective membranes may be employed, as appropriate for particular sensors.

Sensor packages have been built with the construction shown in FIG. 7. When converted to a chloride sensor by converting the silver surface to silver chloride as shown above, they have a calibration curve typical of similar chloride sensors available in the industry, displaying a typical slope of −0.053 millivolts per decade. Also, a sensor for potassium has been built with the package construction shown in FIG. 7. The calibration curve for the potassium sensor displayed a slope of 59 millivolts per decade.

In similar fashion microprocessors may be fashioned from the microprocessor packages for sensing other ions using chemistries well known in the industry. For example, if the hydrogel layer contains an electrolyte solution which has constant concentration of chloride ion, and the membrane contains the appropriate ionophore for potassium ion, an electrochemical potential will be created across the membrane between the sensor and the unknown sample that will depend on the concentration of potassium ions in the unknown. This dependence is described by the Nernst equation. Such hydrogels are available, such as PHEMA, which can be prepared by dissolving hydroxyethyl methacrylate (97%, Aldrich), polyvinylpyrrolidone (Aldrich) and 2,2-dimethoxy-2-phenyl-acetophenne (99%, Aldrich) as photoinitiator in ethylene glycol (99+%, Aldrich). An appropriate ion specific membrane, for instance, can be created by dissolving PVC (Aldrich), potassium tetrakis(4-chlorophenyl)borate (Fluka), (+)-bis(2-ethylthexyl)sebacate (94%, Aldrich), and (+)-valinomycin (90%, Aldrich) as ionophore in a suitable solvent such as Tetrahydrofuran (99.9%, Aldrich) and applying a few drops to the top of the hydrogel, allowing the membrane to dry between applications.

In use the microsensors of this invention may be placed adjacent an external electrical contact, such as in substrate 23 shown in FIG. 14, with the projecting contact 6 pressed thereagainst to provide a stable and secure electrical connection with external circuitry.

Although the description above contains many specificities, these should not be construed as limiting the scope of the invention but as merely providing illustrations of some of the presently preferred embodiments of this invention. Various other embodiments and ramifications are possible within it's scope.

What is claimed is:

1. A chemical sensor package comprising:
   a. A substrate having a front surface and a back surface facing generally away from one another which surfaces extend generally in a common plane and which is comprised of a first non-conductive layer and a second non-conductive layer, the first layer being on the side of the substrate closer to the front surface of the substrate and being comprised of a polymer film,
   b. an electrically conductive trace extending in the plane of the substrate over an area in between the first and second substrate layers and having a front side facing toward the front surface of the substrate, the trace having a three-dimensional conductive circuit feature formed integrally therewith and projecting at least partly through the second non-conductive layer and outwardly of the back surface of the substrate for providing a readily connectable and disconnectable pressure interconnection to another element at said one side of said substrate,
   c. a sensing electrode overlying the trace at an area of trace between the first and second substrate layers and having a front side facing toward the front surface of the substrate and a back side facing toward the back surface of the substrate, the electrode being in electrical contact with the trace and
   d. a well extending into the substrate from the front surface to the front side of the electrode and being exposed to the front side of the electrode.

2. A chemical sensor package comprising:
   a. an electrically conductive copper foil having an upper face and an opposed lower face,
   b. a sensing electrode overlying the foil and having a lower side facing toward the upper face of the foil and in electrical communication with the foil and an opposed upper side facing away from the foil,
   c. a non-conductive overlay overlying and secured to the upper face of the foil and the upper side of the electrode and having an upper surface remote from the foil and electrode and
   d. a well extending into the non-conductive overlay from the upper surface thereof to the upper side of the electrode and being exposed to the upper side of the electrode.

3. A method as in claim 2 and wherein the electrode is comprised of a metal, metal chloride, and/or metal oxide selected from silver, gold, palladium, nickel, platinum, iridium, and their chlorides and oxides.

4. A chemical sensor package as in claim 2 which further comprises a non-conductive underlayer underlying the lower face of the foil and having a lower surface remote from the foil and an opening therethrough at a location adjacent the lower face of the foil, whereby to provide access to the lower face of the foil at said location to permit readily connectable and disconnectable pressure electrical interconnection with another element at the lower surface of the substrate.

5. A chemical sensor for sensing a target chemical which comprises a sensor package as in claim 2 having sensing means in the well of the sensor package capable of electrochemically sensing a target chemical at the well.

6. A chemical sensor package comprising:
   a. electrically conductive foil having an upper face and an opposed lower face,
   b. a sensing electrode overlying the foil and having a lower side facing toward the upper face of the foil and in electrical communication with the foil and an opposed upper side facing away from the foil,
   c. a non-conductive overlay overlying and secured to the upper face of the foil and the upper side of the electrode and having an upper surface remote from the foil and electrode,
   d. a well extending an into the non-conductive overlay from the upper surface thereof to the upper side of the electrode and being exposed to the upper side of the electrode and
   e. a three-dimensional conductive circuit feature formed integrally with the foil that projects below the lower face thereof for providing a readily connectable and disconnectable pressure interconnection to another element below the lower face of the foil.

7. A chemical sensor package as in claim 6 and wherein the foil is comprised of copper.

8. A chemical sensor package as in claim 6 and wherein the foil is comprised of copper and the electrode is comprised of a metal, metal chloride, and/or metal oxide selected from silver, gold, palladium, nickel, platinum, iridium and their chlorides and oxides.

9. A chemical sensor package as in claim 6 and wherein the overlay comprises a polymer film.

10. A chemical sensor package as in claim 9 and wherein the polymer film comprises polyimide film.

11. A chemical sensor for sensing a target chemical which comprises a sensor package as in claim 6 having sensing means in the well of the sensor package capable of electrochemically sensing a target chemical at the well.

12. A chemical sensor as in claim 11 and wherein the electrode is comprised of a metal, metal chloride, and/or metal oxide selected from silver, gold, palladium, nickel, platinum, iridium, and their chlorides and oxides.

13. A chemical sensor as in claim 11 and wherein the foil comprises copper.

14. A chemical sensor as in claim 11 and wherein the sensing means comprises an electrolytic medium.

15. A chemical sensor as in claim 11 and wherein the electrode comprises silver and the sensing means in the well comprises a layer of silver chloride at the upper surface of the electrode.

16. A chemical sensor as in claim 11 and wherein the electrode comprises silver and the sensing means in the well comprises a layer of silver chloride at the upper surface of the electrode and an electrolytic medium comprising chloride ions.

17. A chemical sensor as in claim 11 and including a membrane at the upper surface of the overlay covering the well.

18. A chemical sensor as in claim 17 and wherein the membrane is ion selective to thereby allow potentiometric measurement of voltage between the foil and an analyte external to the well that contains a selected ion.

19. A sensor as in claim 17 and wherein the electrode comprises silver and the sensing means in the well comprises a layer of silver chloride at the upper surface the electrode and an electrolytic medium comprising chloride ions.

20. A chemical sensor as in claim 17 and wherein the electrode is capable of sensing a selected gas and the membrane is permeable to the selected gas to thereby allow potentiometric measurement of voltage between the foil and an analyte external to the well that contains the selected gas.

21. A sensor as in claim 20 and wherein the electrode comprises silver and the sensing means in the well comprises a layer of silver chloride at the upper surface the electrode and an electrolytic medium comprising chloride ions.

22. A generally planar chemical sensor package comprising:
   a. an electrically conductive foil having an upper face and an opposed lower face,
   b. a sensing electrode overlying the foil and having a lower side facing toward the upper face of the foil and in electrical communication with the foil and an opposed upper side facing away from the foil,
   c. a non-conductive overlay overlying and secured to the upper face of the foil and the upper side of the electrode and having an upper surface remote from the foil and electrode,
   d. a well extending into the non-conductive overlay from the upper surface thereof to the upper side of the electrode and being exposed to the upper side of the electrode,
   e. a non-conductive substrate underlying and secured to the lower face of the foil and having a lower surface remote from the foil and
   f. a three-dimensional conductive circuit feature formed integrally with the foil that projects below the lower face thereof, through the non-conductive substrate and outwardly below the lower surface of the substrate for a readily connectable and disconnectable pressure interconnection to another element at the lower surface of the substrate.

23. A chemical sensor package as in claim 22 and wherein the foil is comprised of copper and the electrode is comprised of a metal, metal chloride, and/or metal oxide selected from silver, gold, palladium, nickel, platinum, iridium, and their chlorides and oxides.

24. A chemical sensor package as in claim 22 and wherein the overlay comprises a polymer film.

25. A chemical sensor package as in claim 24 and wherein the polymer film is a polyimide film.

26. A method for forming a chemical sensor package which comprises:
   a. forming a conductive foil having an upper face and an opposed lower face and a three-dimensional conductive circuit feature formed integrally therewith that projects below the lower face thereof at a location on the foil for providing a readily connectable and disconnectable pressure interconnection to another element below the lower face of the foil,
   b. forming a sensing electrode on the foil with a lower side thereof facing toward the upper face of the foil and in electrical communication with the foil and an opposed upper side facing away from the foil and
   c. overlaying the upper face of the foil and the upper side of the electrode with a non-conductive overlayer, the overlayer having an upper surface remote from the foil and the electrode and having a well extending through the overlay from the upper surface thereof to the upper side of the electrode and being exposed to the upper side of the electrode.

27. A method as in claim 26 and including the further step of underlaying the lower face of the foil with a non-conductive underlayer having a lower surface remote from the roil and an opening therein at the location where the three-dimensional circuit feature of the foil projects below the lower face thereof, whereby to permit the circuit feature to project therethrough and downwardly below the lower surface of the underlayer for providing the readily connectable and disconnectable pressure interconnection to another element at the lower surface of the substrate.

28. A method as in claim 27 and wherein the electrode is comprised of a metal, metal chloride, and/or metal oxide selected from silver, gold, palladium, nickel, platinum, iridium, and their chlorides and oxides.

29. A method as in claim 27 and wherein the foil comprises copper.

30. A method as in claim 27 and wherein the overlay comprises a polymer film.

31. A method as in claim 30 and wherein the polymer film comprises a polyimide film.

32. A method of forming a chemical sensor package which comprises:
   a. providing a mandrel having an electrically conductive surface configured to produce a foil when a conductive metal is electrodeposited thereupon, the surface having a depression therein,
   b. electrodepositing a conductive metal on the electrically conductive surface to form a foil having a lower face adjacent the mandrel surface and an opposed upper face remote from the mandrel surface and, at the depression in the mandrel surface, a three-dimensional circuit feature formed integrally therewith that project below the lower face thereof at a location on the foil for providing a readily connectable and disconnectable pressure interconnections to another element below the lower face of the foil,
   c. forming an electrode on the upper surface of the foil with the electrode having a lower surface adjacent and in electrical contact with the foil and an opposed upper surface,
   d. laminating a non-conductive coverlayer onto the upper surface of the foil and of the electrode on the mandrel, the non-conductive coverlayer having an lower surface adjacent the upper face of the foil and an opposed upper surface and having an opening therethrough at the location of the electrode, whereby to form a well extending from the upper surface of the cover layer to the upper surface of the electrode and e. separating the laminated coverlayer and foil from the mandrel.

33. A method as in claim 32 and including the further step of underlaying the lower face of the foil with a non-conductive underlayer having a lower surface remote from the foil and an opening at the location where the three-dimensional circuit feature of the foil projects below the lower face thereof, whereby to permit the circuit feature to project therethrough and downwardly below the lower surface of the underlayer for providing the readily connectable and disconnectable pressure interconnection to another element at the lower surface of the substrate.

34. A method as in claim 32 and wherein the conductive metal is comprised of copper and the electrode is comprised of a metal, metal chloride, and/or metal oxide selected from silver, gold, palladium, nickel, platinum, iridium, and their chlorides and oxides.

35. A method as in claim 32 and wherein the overlay comprises a polymer film.

36. A method as in claim 35 and wherein the polymer film comprises a polyimide film.

37. A method for forming a chemical sensor package which comprises:

a. forming a conductive copper foil having an upper face and an opposed lower face, b. forming a sensing electrode on the foil with a lower side thereof facing toward the upper face of the foil and in electrical communication with the foil and an opposed upper side facing away from the foil and c. overlaying the upper face of the foil and the upper side of the electrode with a non-conductive overlayer, the overlayer having an upper surface remote from the foil and the electrode and having a well extending through the overlay from the upper surface thereof to the upper side of the electrode and being exposed to the upper side of the electrode.

38. A method as in claim 37 and wherein the electrode is comprised of a metal, metal chloride and/or metal oxide selected from silver, gold, palladium, nickel, platinum, iridium, and their chlorides and oxides.

39. A method as in claim 37 and including the further step of underlaying the lower face of the foil with a non-conductive underlayer having a lower surface remote from the foil and an opening therein at a location adjacent the lower face of the foil for providing access for a readily connectable and disconnectable pressure interconnection to another element at the lower surface of the substrate.

40. A method as in claim 39 and wherein the conductive metal is comprised of copper and the electrode is comprised of a metal, metal chloride, and/or metal oxide selected from silver, gold, palladium, nickel, platinum, iridium, and their chlorides and oxides.

41. A method of forming a chemical sensor package which comprises:

a. providing a mandrel having an electrically conductive surface configured to produce a foil when a conductive metal is electrodeposited thereupon, b. electrodepositing a conductive metal on the electrically conductive surface to form a foil having a lower face adjacent the mandrel surface, c. forming an electrode on the upper surface of the foil with the electrode having a lower surface adjacent and in electrical contact with the foil and an opposed upper surface, d. laminating a non-conductive coverlayer onto the upper surface of the foil and of the electrode on the mandrel, the non-conductive coverlayer having an lower surface adjacent the upper face of the foil and an opposed upper surface and having an opening therethrough at the location of the electrode, whereby to form a well extending from the upper surface of the cover layer to the upper surface of the electrode and e. separating the laminated coverlayer and foil from the mandrel.

42. A method as in claim 41 and including the further step of underlaying the lower face of the foil with a non-conductive underlayer having a lower surface remote from the foil and an opening therethrough at a location adjacent the lower face of the foil, whereby to provide access to the lower face of the foil at said location to permit readily connectable and disconnectable pressure electrical interconnection with another element at the lower surface of the substrate.

* * * * *

UNITED STATES PATENT AND TRADEMARK OFFICE
CERTIFICATE OF CORRECTION

PATENT NO. : 6,849,168 B2
DATED : February 1, 2005
INVENTOR(S) : William F. Crumly et al.

It is certified that error appears in the above-identified patent and that said Letters Patent is hereby corrected as shown below:

Title page
Item [73], Assignee, "KVAL, Inc., Petaluma, CA (US)" should read -- MicroBionics, Inc., 275 Shoreline Drive, Suite 150, Redwood City, CA 94065 (US) --.

Signed and Sealed this

Twenty-second Day of November, 2005

JON W. DUDAS
*Director of the United States Patent and Trademark Office*